US006962151B1

(12) United States Patent
Knoch et al.

(10) Patent No.: US 6,962,151 B1
(45) Date of Patent: Nov. 8, 2005

(54) INHALATION NEBULIZER (75) Inventors: Martin Knoch, Berg (DE); Manfred Keller, Bad Krozingen (DE); Roland Stangl, Moosburg (DE); Thomas Gallem, Munich (DE); Rainer Liening-Ewert, Alfausen (DE); Markus Urich, Munich (DE)

(73) Assignee: Pari GmbH Spezialisten für effektive Inhalation, Starnberg (DE)

( * ) Notice: Subject to any disclaimer, the term of this patent is extended or adjusted under 35 U.S.C. 154(b) by 0 days.

(21) Appl. No.: 10/129,498

(22) PCT Filed: Oct. 27, 2000

(86) PCT No.: PCT/US00/29541

§ 371 (c)(1), (2), (4) Date: Sep. 19, 2002

(87) PCT Pub. No.: WO01/34232

PCT Pub. Date: May 17, 2001

(30) Foreign Application Priority Data

Nov. 5, 1999 (DE) ............................... 199 53 317

(51) Int. Cl.[7] ....................... A61M 11/00; A61M 11/06

(52) U.S. Cl. ........................... 128/200.14; 128/200.16; 239/338; 239/102.2

(58) Field of Search ...................... 128/200.14, 200.16, 128/200.23, 200.17, 200.18, 200.22; 239/338, 239/102.2

(56) References Cited

U.S. PATENT DOCUMENTS 3,387,607 A * 6/1968 Gauthier et al. ....... 128/200.16
4,001,650 A * 1/1977 Romain ...................... 361/106
4,093,124 A 6/1978 Morane et al.
4,113,809 A * 9/1978 Abair et al. .................. 261/81
4,334,531 A * 6/1982 Reichl et al. .......... 128/200.14
4,582,654 A * 4/1986 Karnicky et al. ............ 261/91
4,702,418 A * 10/1987 Carter et al. ................ 239/101
4,819,629 A * 4/1989 Jonson .................. 128/203.22
4,823,784 A * 4/1989 Bordoni et al. ........ 128/200.14
4,877,989 A * 10/1989 Drews et al. .......... 310/323.01
4,976,259 A * 12/1990 Higson et al. ......... 128/200.18
5,054,477 A 10/1991 Terada et al.
5,134,993 A * 8/1992 van der Linden et al. ..................... 128/200.14
5,435,282 A 7/1995 Haber et al.
5,479,920 A * 1/1996 Piper et al. ............ 128/204.23
5,503,139 A 4/1996 McMahon et al.
5,533,501 A 7/1996 Denyer
5,579,757 A 12/1996 McMahon et al.
5,586,550 A 12/1996 Ivri et al.
5,617,844 A * 4/1997 King ..................... 128/200.18
5,758,637 A 6/1998 Ivri et al.
5,848,587 A * 12/1998 King ..................... 128/200.18
5,875,774 A 3/1999 Clementi et al.
5,918,593 A * 7/1999 Loser .................... 128/200.16
5,970,974 A * 10/1999 Van Der Linden et al. ..................... 128/200.16
6,062,212 A * 5/2000 Davison et al. ........ 128/200.16

(Continued)

*Primary Examiner*—Mital Patel
(74) *Attorney, Agent, or Firm*—Merchant & Gould P.C.

(57) ABSTRACT

An inhalation nebulizer (1) includes an aerosol generator (2) that has a diaphragm (22) vibrated by a vibration generator (23). The inhalation nebulizer (1) includes a liquid storage container (21) that is in fluid contact with the diaphragm (22). A liquid contained in the storage container (21) is atomized into a mixing chamber (3) through openings in the diaphragm and can subsequently be inhaled by a patient.

48 Claims, 5 Drawing Sheets

U.S. PATENT DOCUMENTS

| | | |
|---|---|---|
| 6,085,740 A | 7/2000 | Ivri et al. |
| 6,247,525 B1 * | 6/2001 | Smith et al. ........... 165/104.25 |
| 6,427,682 B1 * | 8/2002 | Klimowicz et al. .... 128/200.16 |
| 6,439,474 B2 * | 8/2002 | Denen ..................... 239/102.2 |
| 6,640,804 B2 * | 11/2003 | Ivri et al. .............. 128/200.16 |
| 6,651,650 B1 * | 11/2003 | Yamamoto et al. .... 128/200.16 |

* cited by examiner

200
INHALATION NEBULIZER

TECHNICAL FIELD

The invention relates generally to inhalation nebulizers and more specifically to inhalation nebulizers which form aerosols of liquid pharmaceuticals and liquids that contain pharmaceuticals. More specifically, the invention relates to inhalation nebulizers that form such aerosols medicaments while minimizing aerosol losses.

BACKGROUND

Inhalation nebulizers deliver therapeutically effective amounts of pharmaceuticals by forming an aerosol which includes particles of a size that can easily be inhaled. The aerosol can be used, for example, by a patient within the bounds of an inhalation therapy, whereby the therapeutically effective pharmaceutical or drug reaches the patient's respiratory tract upon inhalation.

A variety of inhalation nebulizers are known. EP 0 170 715 A1 uses a compressed gas flow to form an aerosol. A nozzle is arranged as an aerosol generator in an atomizer chamber of the inhalation nebulizer and has two suction ducts arranged adjacent a compressed-gas channel. When compressed air flows through the compressed-gas channel, the liquid to be nebulized is drawn in through the suction ducts from a liquid storage container.

Figure 1A:
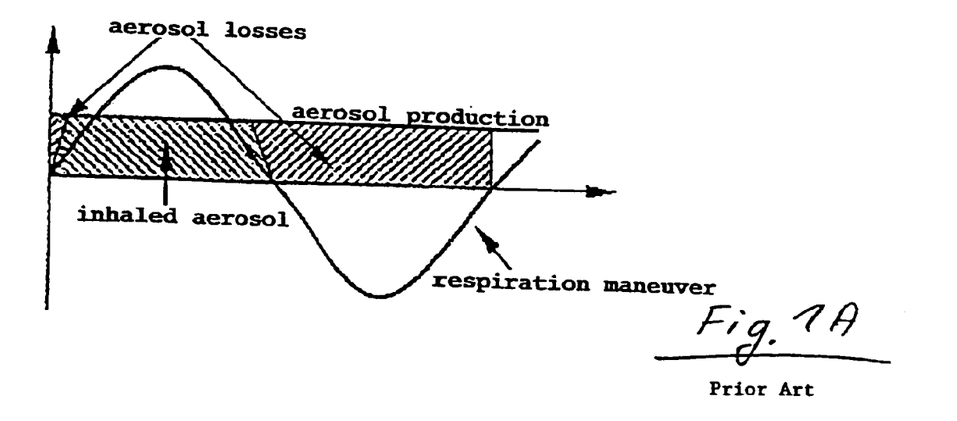
FIG. 1A shows a time history of continuous aerosol production with respect to a respiration cycle according to the prior art.

This nebulizer is representative of continuously operating inhalation nebulizers, in which the aerosol generator produces an aerosol not only during inhalation but also while the patient exhales. This is represented schematically in FIG. 1A, in which a respiration cycle consisting of an inhalation phase and an exhalation phase is shown. The aerosol produced by the aerosol generator is actually inhaled by the patient only in the inhalation phase, while any aerosol produced at other times is lost.

Figure 1B:
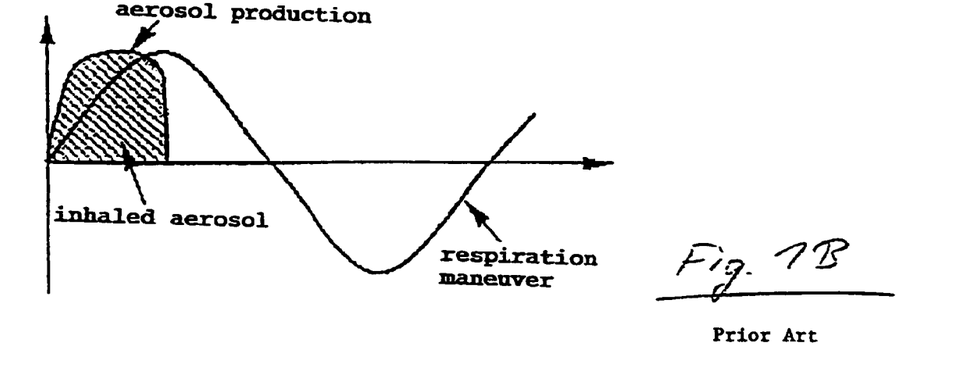
FIG. 1B shows a time history of controlled aerosol production with respect to a respiration cycle according to the prior art.
Figure 2:
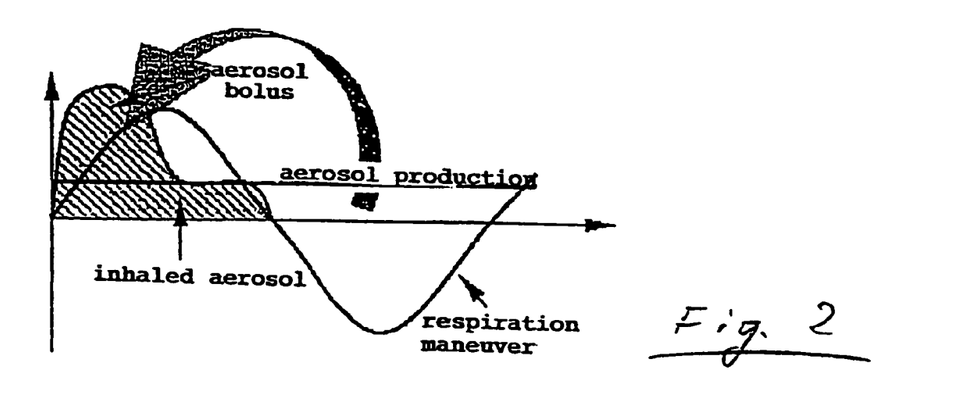
FIG. 2 shows the time history of a respiration cycle during continuous aerosol production according to the invention.

In order to avoid aerosol losses, attempts have been made to restrict aerosol production to part or all of the inhalation phase, thereby obtaining the course schematically represented in FIG. 1B. Either a patient can interrupt aerosol production manually, or the patient's respiration can be detected by sensors that automatically control aerosol production. Neither situation is flawless, as manual control of aerosol production is an additional strain for patients and often leads to insufficient results. Automatic control of aerosol production represents an enormous technical expenditure which as a rule bears little relation to the obtained benefit.

Thus, a need remains for an inhalation nebulizer by means of which, with a low constructional expenditure, an increased amount of aerosol can be provided in the inhalation phase, while at the same time the aerosol losses during the exhalation phase can be reduced.

SUMMARY OF THE INVENTION

The invention involves an inhalation nebulizer having both an aerosol generator and a mixing chamber. The aerosol generator includes a liquid storage container for a liquid medicament. In this, a liquid medicament can be a drug that is itself a liquid, or the liquid medicament can be a solution, suspension or emulsion that contains the medicament of interest. In a preferred embodiment, the liquid medicament is an active agent that is in a solution, a suspension or an emulsion.

The aerosol generator also includes a diaphragm that is connected on one side to the liquid storage container such that a liquid contained in the liquid storage container will come into contact with one side of the diaphragm. The diaphragm is connected to a vibration generator that can vibrate the diaphragm so that a liquid in the liquid storage container can be dispensed or dosed for atomization through openings present in the diaphragm and enter the mixing chamber.

The mixing chamber has an inhalation valve that allows ambient air to flow into the mixing chamber during an inhalation phase while preventing aerosol from escaping during an exhalation phase. The mixing chamber also has an exhalation valve that allows discharge of the patient's respiratory air during the exhalation phase while preventing an inflow of ambient air during the inhalation phase.

DETAILED DESCRIPTION OF PREFERRED EMBODIMENTS

According to a preferred embodiment of the invention, the aerosol generator continuously produces an aerosol. The aerosol is collected in the mixing chamber while the patient exhales into the inhalation nebulizer. The exhalation valve ensures that the patient's exhaled air is vented to the surroundings without significantly reaching the mixing chamber, while the inhalation valve is closed during the exhalation phase and prevents the aerosol from escaping the mixing chamber. During the exhalation phase, the continuously operating aerosol generator accumulates or concentrates the aerosol in the mixing chamber so that during an inhalation phase not only the amount of aerosol generated due to the continuous production is available for the inhalation, but that at the beginning of the inhalation phase an aerosol bolus can be inhaled, which is available because of aerosol accumulation during the exhalation phase.

Here the invention takes advantage of the special characteristics of the atomization of a liquid by an aerosol generator, in particular of the comparatively low speed and good respirability of the aerosol particles directly after generation. Consequently, the aerosol bolus formed during the exhalation phase rapidly stabilizes, i.e. aerosol particle size does not significantly change as a result of evaporation, as the volume of the mixing chamber being available to the amount of aerosol is relatively small and according to the invention practically no ambient air reaches the mixing chamber during the exhalation phase in which the aerosol for the aerosol bolus is generated.

In a preferred embodiment, the diaphragm forms a part of the wall of the liquid storage container so that a liquid within the liquid storage container directly contacts the diaphragm, thereby ensuring continuous aerosol generation. Preferably, the vibration generator is a piezoelectric element.

The exhalation valve can be arranged at the mixing chamber, i.e. in the wall of the mixing chamber. Preferably, the exhalation valve is located near to where the respiratory air of the patient arrives in the inhalation nebulizer. In a preferred embodiment, the exhalation valve is located near the mouthpiece or the mouth piece connection. In order to discharge exhalation air as directly as possible to the environment, in another advantageous development the exhalation valve is arranged in or at the mouthpiece itself which is removably mounted at the mixing chamber and through which the patent inhales the aerosol from the mixing chamber. In this case the mouthpiece can be designed such that it enlarges the mixing chamber and provides additional volume. At the same time the arrangement of the exhalation valve in the mouthpiece permits the valve to lie near the mouthpiece opening, which additionally contributes to a direct discharge of the exhalation air into the surroundings.

In a further advantageous aspect the liquid storage container is a cylinder, the aerosol producing diaphragm is arranged as one side of the cylinder is a circular disk, and the vibration generator is a circular ring surrounding the diaphragm. In this design, ambient air is fed into the mixing chamber through an annular space or gap lying concentrically to the cylinder axis of the liquid storage container. Preferably, a valve element of the inhalation valve also is designed as a circular disk.

Figure 6:
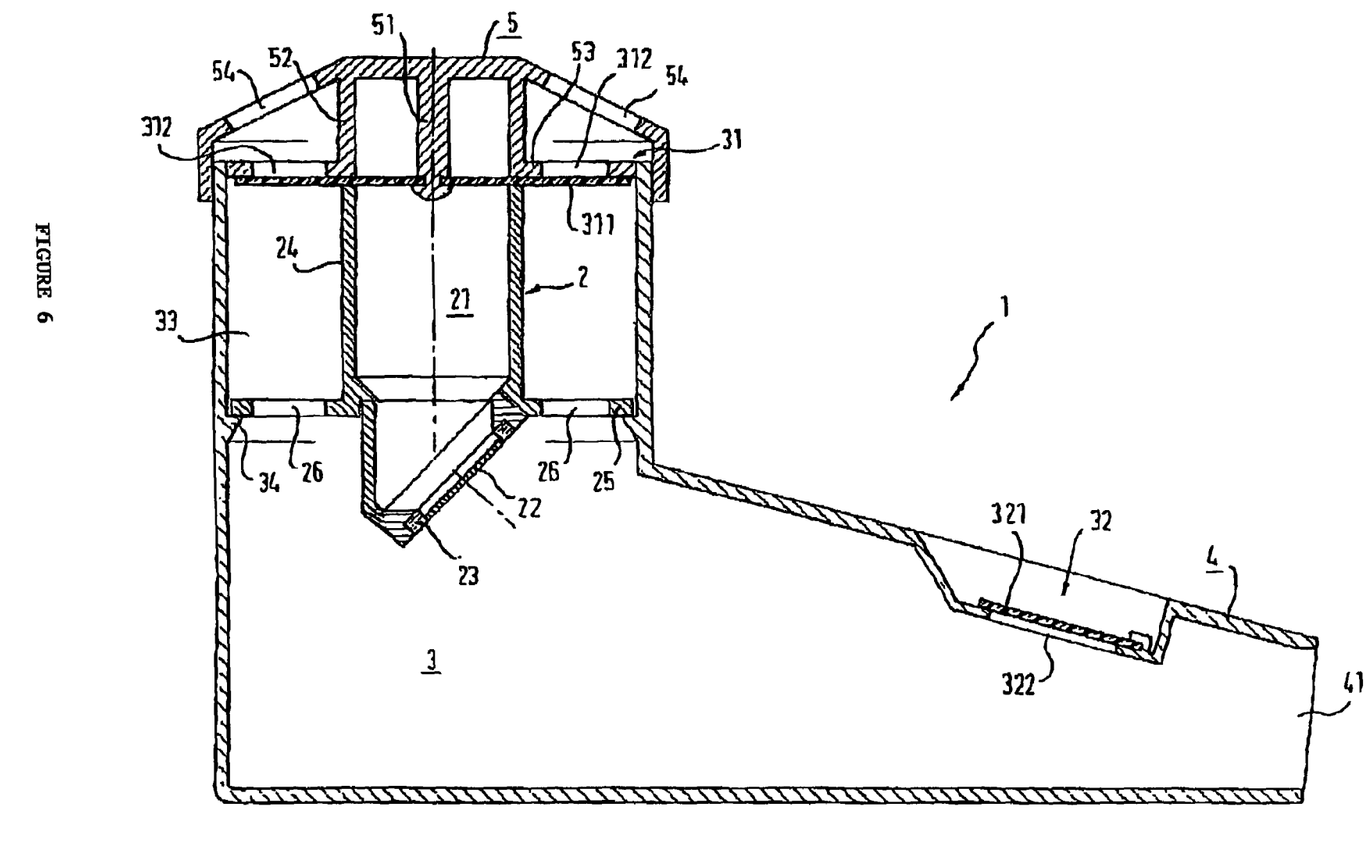
FIG. 6 shows a sectional view of an embodiment of an inhalation nebulizer according to the invention.

Principally, the rotationally symmetrical design of the aerosol generator and also of the mixing chamber, at least in the section receiving the aerosol generator, is advantageous. The diaphragm can be positioned perpendicular to the axis of rotation (FIG. 3), but it also can be inclined thereto (FIG. 6).

As in the inventive inhalation nebulizer the aerosol production can be carried out continuously, no technically expensive control of the aerosol generator is required. But, nevertheless, an almost optimal course of the aerosol production and provision for the patient can be obtained, as in particular at the beginning of the inhalation phase an aerosol bolus is provided.

The aerosol nebulizer described herein can be used to deliver a variety of different active agents. Any drug that can be provided in a solution, a suspension or an emulsion can be delivered as an active agent via the aerosol nebulizer, which offers the possibility of topical and/or systemic drug delivery, depending on the particle size distribution achieved.

The particle size distribution can be tailored to a particular application. For example, a mass median aerodynamic diameter (MMAD) greater than about 10 $\mu$m is preferred for delivering drugs to a patient's nasal passages. Conversely, for pulmonary application, MMAD values less than about 10 $\mu$m and particularly below about 6 $\mu$m are preferred. Particles below about 3 $\mu$m in size can be generated for deep lung and systemic drug delivery with the nebulizer described herein.

By way of example, topical pulmonary drug administration can be used to treat diseases such as asthma, chronic obstructive pulmonary diseases, lung infections, lung cancer, cystic fibrosis and others.

The aerosol nebulizer can also be used to deliver drugs that cannot be administered orally due to lack of solubility and bio-availability or poor absorption or degradation of drugs in the gastrointestinal tract. Furthermore, the nebulizer can be used for the systemic administration of drugs which usually require parenteral administration by the intravenous (iv.), intramuscular (im), subcutaneous (sc), and intrathekal route.

Hence, the aerosol nebulizer allows both topical and systemic aerosol drug delivery via either the nasal or the pulmonary route for a wide variety of drugs that can be formulated or prepared in-situ or immediately before use as solution, suspension or emulsion or any other pharmaceutical application system, such as liposomes or nanosomes. The nebulizer can be modified with respect to the pore size and dimension of the mixing chamber to direct aerosol delivery either into the nose or lungs. Therefore, various droplet and particle sizes can be generated which can deliver aerosols with MMADs from 1 to 30 $\mu$m.

Various drugs can be administered as formulations with immediate or controlled drug release irrespective of whether or not the drug is coated by an excipient. Alternatively, the drug can be formulated as a vesicle such as a liposome or nanosome, or as a micro and/or nanaocapsule. The nebulizer is useful for the application of nearly all therapeutic drug classes alone or in combinations. Drugs can be formulated as any pharmaceutical acceptable derivative or salt. Chiral drugs can be used as isomers, diastereomers, or racemic mixtures. Examples of therapeutic classes and drug categories are listed below:

anti-asthmatics include beta-agonists such as salbutamol, levalbuterol, formoterol, fenoterol, salmeterol, bambuterol, brocaterol, clenbuterol, terbutalin, tulobuterol, epinephrin, isoprenalin, and hexoprenalin;

anti-cholinergics, including tiotropium, oxitropium, ipratropium, glcopyrrolate;

corticosteroids, elastane-, leucotriene-, and bradykininantagonists;

mucolytics and surfactants such as acetylcystein, ambroxol, carbocystein, tyloxapol, dipalmytoylphosphatidylcholin, recombinant surfactant proteins, and D-Nase;

anti-inflammatory drugs including mediator cell inhibitors such as romoglycate and nedocromil, corticostroids such as beclomethasone, betamethasone, budesonide, ciclesonide, flunisolide, fluticasone, icomethasone, mometasone, rofleponide, triamcinolone, bradykinine-, prostaglandine-, leucotriene- and platelet activating factor antagonists;

a wide variety of antibiotics, such as:

beta-lactam antibiotics, including amoxycillan, piperacillin, clavulan acid, and sulbactam, cephalosporines, including cefaclor, cefazedon, Cefuroxim, Cefoxitin, cefodizim, cefsulodin, cefpodixim, and cefixim, carbapenemes such as imipenem and cilastatin, monbactames such as aztrenonam, aminoglycosides, including streptomycin, neomycin, paromomycin, kanamycin, gentamycin, amicacin, tobramycin, and spectinomycine, tetracyclines such as doxycyclin and minocycline, macrolides including erythromycine, clarithromycine, roxithromycine, azithromycine, josamycine, and spiramycine, gyrase inhibitors or quinolones such as Ciprofloxacin, Ofloxacine, Levofloxacine, pefloxacine, lomefloxacine, fleroxacine, clinafloxacine, sitafloxacine, gemifloxacine, balofloxacine, trovafloxacine, and moxifloxacine, sulfonamides and nitroimidazoles including metronidazol, tinidazol), chloramphenicol, lincomycine, clindamycine, and fosfomycine, and glycopeptides such as Vancomycine and Teicoplanine;

anti-tuberculostatics such as rifampicine, isoniacide, cycloserine, terizidone, and ansamycine;

anti-mycotics and anti-fungals, including azol derivatives such as clotrimazol, oxiconazol, miconazol, ketoconazol, itraconazol, and fluconazol, polyen-antibiotics such as amphotericine B, natamycine, nystatine, and flucytosine, and chemotherapeutics such as Pentamidine;

immunsuppresors and immunemodulators, cytokines (dimepranol-4-acetate amideo benzoate, thymopentin, interferones, filgrastine, interleukine, azathioprine, and ciclosporine;

virustatics such as podophyllotoxine, vidarabine, tromantadine, and zidovudine, and proteinase-inhibitors such as a-anti-trypsin;

anti-oxidants such as tocopherols and glutathion; pituitary hormones, hypothalamic hormones, regulatory peptides and their inhibiting agents such as corticotropine, tetracosactide, choriogonandotropine, urofolitropine, urogonadotropine, saomatotropine, metergoline, desmopressine, oxytocine, argipressine, ornipressine, leuproreline, triptoreline, gonadoreline, busereline, nafareline, goselerine, and somatostatine;

parathyroide gland hormones, calcium metabolism regulators such as Dihydrotachysterole, calcitonine, clodron acid, etidron acid, and thyroid gland therapeutics;

sex hormones and their inhibiting agents, such as anabolics, androgens, etrogens, gestagenes, and antiestrogenes;

cytostatics and metastasis inhibitors such as:

alkylants including nimustine, melphanlane, carmustine, lomustine, cyclophosphamide, ifosfamide, trofosfamide, chlorambucil, busulfane, treosulfane, prednimustine, and thiotepa, anti-metabolites such as cytarabine, fluorouracil, methotrexate, mercaptopurine, and tioguanine, alkaloids including vinblastine, vincristine, and vindesine, antibiotics such as alcarubicine, bleomycine, dactinomycine, daunorubicine, doxorubicine, epirubicine, idarubicine, mitomycine, and plicamycine, complexes of secondary group elements (e.g. Ti, Zr, V, Nb, Ta, Mo, W, Pt) such as carboplatinum, cisplatinum and metallocene compounds such as titanocendichloride Amsacrine, dacarbazine, estramustine, etoposide, hydroxycarbamide, mitoxanthrone, procarbazine, and temiposide;

migraine agents including Proxibarbal, lisuride, methysergide, dihydroergotamine, ergotamine, clonidine, pizotifene;

hypnotics and sedatives such as bezodiazepines, barbiturates, cyclopyrrolones, and imidazopyridines;

anti-epileptics including barbiturates, Pheytoin, Primidone, mesuximide, ethosuximide, sultiam, carbamazepin, valproic acid, vigabatrine;

anti-Parkinson drugs such as Levodopa, carbidopa, benserazide, selegiline, bromocriptine, amantadine, and tiapride;

Anti-emetics including Thiethylperazine, bromopride, domperidone, granisetrone, ondasetrone, tropisetrone, and pyridoxine;

central acting analgesics such as morphine, codeine, hydromorphone, methadone, fenpipramide, fentanyl, piritramide, pentazocine, buprenorphine, nalbuphine, and tilidine;

drugs for narcosis including N-methylated barbiturates, thiobarbiturates, ketamine, etomidate, propofol, benzodiazepines, droperidol, haloperidol, alfentanyl, and sulfentanyl;

anti-rheumatics such as tumor necrosis factor alpha and non steroidal anti-inflammatory drugs;

anti-diabetic drugs including insulin, sulfonylurea derivatives, biguanids, glitizols, glucagon, and diazoxid;

cytokines, such as interleukines, interferones, tumor necrosisfactor (TNF), and colony stimulating factors (GM-CSF, G-CSF, M-CSF)

proteins (e.g. erythropoetine) and peptides (e.g. parathyrin, somatomedin C) or other drugs such as heparine, heparinoids, urokinases, streptokinases, ATP-ase, prostacycline, sexual stimulants, or genes, which cannot be administered orally can be delivered advantageously by the inventive nebulizer either by the nasal or pulmonary route.

Figure 3:
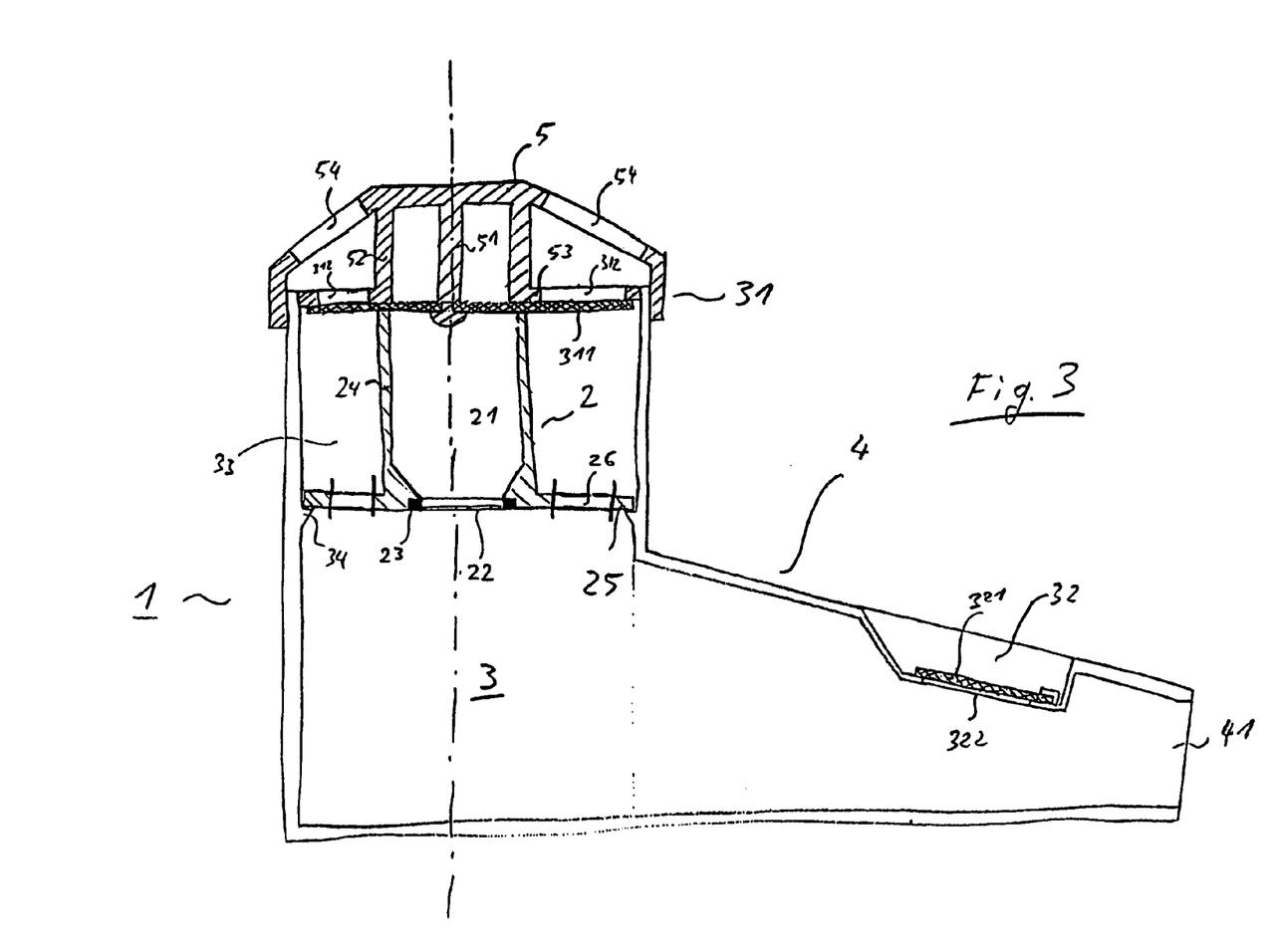
FIG. 3 shows a sectional view of an embodiment of an inhalation nebulizer according to the invention.

Referring to the construction illustrated in FIG. 3 as one example of the present invention, the aerosol generator 2 includes a cylindrical liquid storage container 21 that is defined on one side by a diaphragm 22 that preferably is a circular disk. A liquid (not shown) filled in the liquid storage container contacts one side of the diaphragm 22. A vibration generator 23, for instance a piezoelectric crystal, surrounds the diaphragm 22 circumferentially such that the diaphragm 22 can be vibrated by the vibration generator 23. This requires a (not shown) electric drive circuit for the vibration generator, the structure and function of which are well known to the person skilled in this art.

Through openings present in the diaphragm 22, the liquid adjoining one side of the diaphragm 22 is atomized through to the other side of the diaphragm 22 and thus is atomized into the mixing chamber 3.

The liquid storage container 21 preferably provides an entry point for the articular medicament to be dispensed. In one embodiment, the liquid storage container 21 is a liquid reservoir that is directly fitted into the inhalation nebulizer 1. In another embodiment, the medicament is provided to the liquid storage container 21 as a metered volume from either a single dose or multi dose container. If a multi dose container is used, it is preferably equipped with a standard metering pump system as used in commercial nasal spray products.

If the liquid storage container 21 is cylindrical, it is preferred that the diaphragm 22 has a circular design and the vibration generator 23 has an annular design. The inhalation nebulizer 1 includes an aerosol generator 2 and a mixing chamber 3 having an inhalation valve 31 and an exhalation valve 32.

Preferably, the aerosol generator 2 is arranged in a section of the mixing chamber 3 that is also of a cylindrical design. Thereby an annular gap 33 is obtained around the aerosol generator 2 through which the ambient air can flow into the mixing chamber 3 during the inhalation phase.

A mouthpiece 4 is preferably integrally formed with the mixing chamber 3, but it also can be attached removably to the mixing chamber. A patient inhales the aerosol through the mouthpiece 4. The aerosol is generated by the aerosol generator 2 and is stored in the mixing chamber 3. The size and the form of the mouthpiece 4 can be chosen such that it enlarges the mixing chamber 3 and simultaneously provides for the arrangement of the exhalation valve 32. The exhalation valve is preferably located adjacent the opening 41 of the mouthpiece 4 facing the patient.

When a patient exhales into the opening 41 of the mouthpiece 4, the exhalation valve 32 is opened so that the respiratory air of the patient is discharged into the surroundings. To this end, a valve element 321 of the exhalation valve 32 is lifted and frees the opening 322 of the exhalation valve 32. The inhalation valve 31 is closed when the patient exhales into the inhalation nebulizer, as the valve element 311 of the inhalation valve 31 closes the opening 312 of said valve.

When a patient inhales through the opening 41 of the mouthpiece 4, the inhalation valve 31 is opened and frees the opening 312 as the valve element 311 is lifted. Thereby ambient air flows through the inhalation valve 31 and the annular gap 33 into the mixing chamber 3 and is inhaled by the patient together with the aerosol. As aerosol has accumulated in the mixing chamber 3 during an exhalation phase, there is available to the patient an increased amount of aerosol, a so-called aerosol bolus, especially at the beginning of an inhalation phase.

In a preferred embodiment, the inhalation valve is adapted to the cylindrical form of the aerosol 2 and the annular gap 33. The flexible valve element 311 is formed as a circular disk that is attached at a centrally arranged fastening projection 51 of a cap 5 mounted at, e.g. screwed on, the cylindrical section of the mixing chamber 3. The cap 5 also has a cylindrical connecting piece 52 which, in interaction with the outer wall 24 of the liquid storage container 21, clamps and fastens the valve element 311.

At the side of the cylinder connecting piece 52 facing the liquid storage container 21 there is also integrally formed a first circular ring disk 53 in which the openings 312 of the inhalation valve 31 are defined. Corresponding openings 54 are provided in cap 5 so that ambient air can flow through the openings 54 and 312 into the mixing chamber 3 during an inhalation process. At the front side comprising the diaphragm the aerosol generator 2 has a second circular ring disk 25 with openings 26 through which the ambient air flows during the inhalation phases. The circular ring disk 25 rests upon a projection 34 formed at the inner wall of the cylindrical section of the mixing chamber 3. Thus, when the cap 5 is positioned thereupon or screwed thereon, the aerosol generator 2 as well as the flexible valve element 311 of the inhalation valve 31 are securely fixed.

Apart from the above described cylindrical design of the aerosol diaphragm generator and of a section of the mixing chamber, other rotationally symmetrical designs can advantageously be used. Furthermore, the diaphragm of the aerosol generator can also be arranged in an inclined position whereby the spreading of the aerosol generated by the aerosol diaphragm generator can be influenced and thus, with regard thereto, the specific design of the mixing chamber and also of the mouthpiece can be optimized.

The following non-limiting examples are intended only to illustrate the present invention.

WORKING EXAMPLE 1

The inhalation nebulizer described herein was used to test the atomization of two commercial products along with a novel submicron suspension. A salbutamol-sulfate solution available commercially as VENTOLIN™ (known generically as albuterol) was tested, as was a budesonide suspension sold under the name PULMICORT™. For comparison purposes, a novel submicron suspension of budesonide was also tested. Each solution or suspension was tested during continuous mode and during breath-triggered mode to evaluate the performance of the inhalation nebulizer.

Evaluation included looking at the percent of the test solution available for capture by an inhalation filter, as well as looking at product that remained in the mixing chamber, the fluid feed, or was otherwise lost or unrecoverable.

Figure 4:
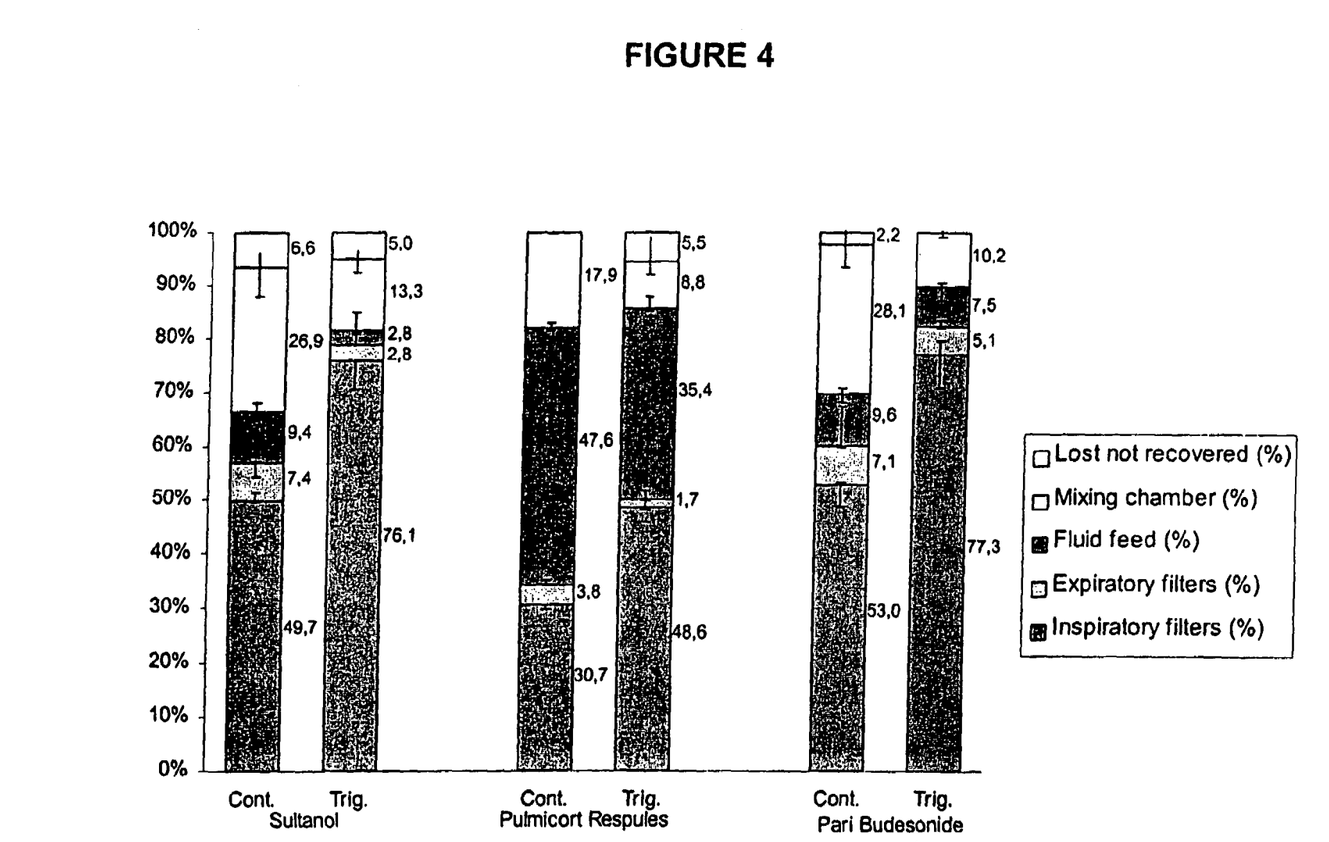
FIG. 4 shows the performance of several known drugs and a novel submicron suspension when dispensed with a nebulizer according to the invention.

The results are depicted graphically in FIG. 4. The results indicate that deposition to an inhalation filter can be increased from about 50 percent to about 75 percent by operating in the breath-triggered mode if dispensing either the albuterol solution or the novel submicron budesonide suspension. An efficiency of about 50 percent can be achieved by dispensing the commercial budesonide suspension in breath-triggered mode.

WORKING EXAMPLE 2

Figure 5:
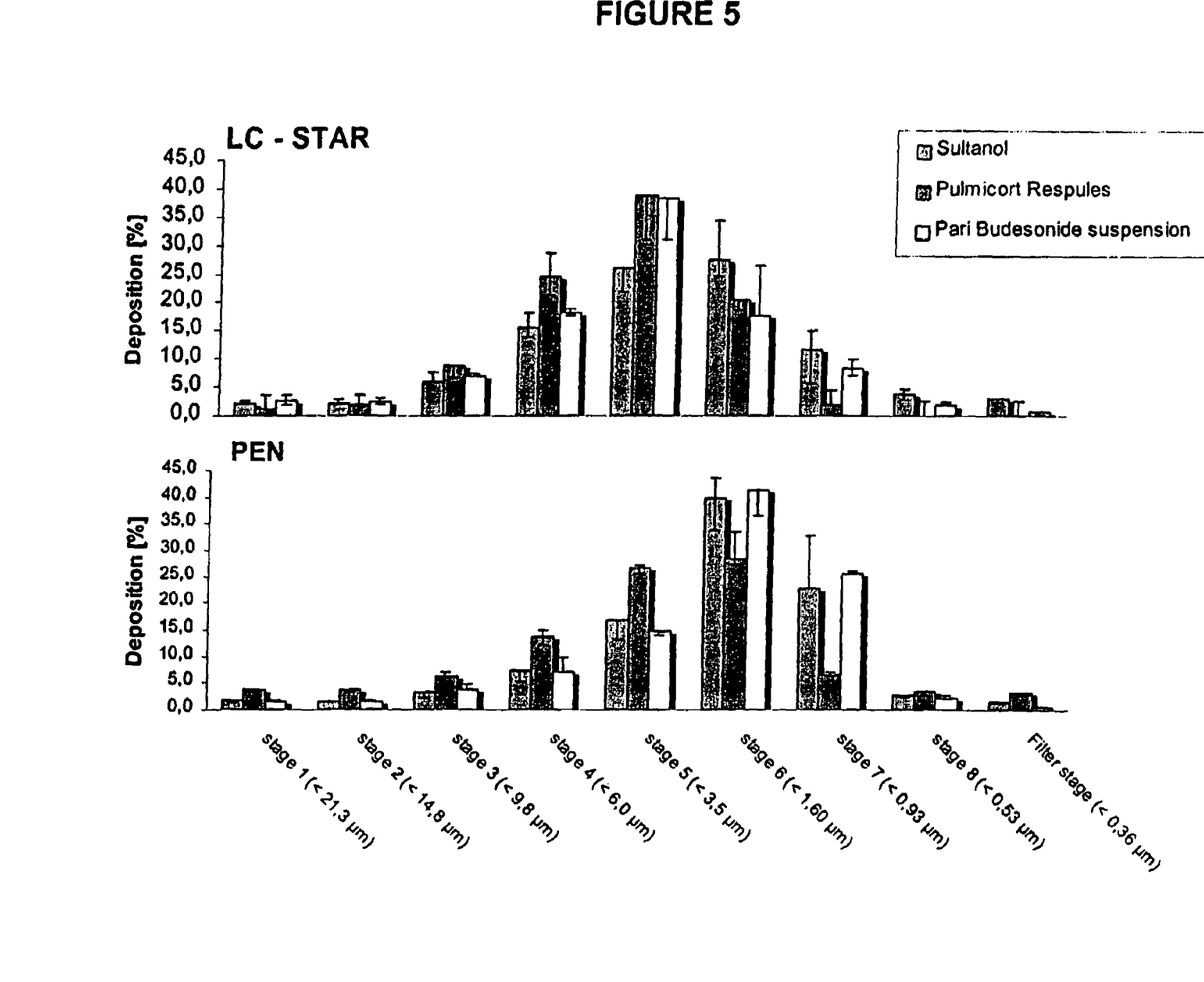
FIG. 5 compares the aerodynamic particle size performance of a nebulizer according to the invention with an existing product.

The inhalation nebulizer described herein was tested against a commercially available product (the PARI LC STAR) using the three test components described in the previous Example. FIG. 5 provides results for the LC STAR and the results achieved by the inventive nebulizer (PEN). The results clearly indicate that the nebulizer in accordance with the invention provides for a higher proportion of drug available at smaller average particle sizes. Specifically, the MMAD is shifted from about 3.7 to 5.11 $\mu$m (for the PARI LC STAR) to about 2.2 to 3.9 $\mu$m for the inventive nebulizer.

The above specification, data and examples provide an enabling description of the manufacture and use of the invention. Since many embodiments of the invention can be made without departing from the spirit and scope of the invention, the invention resides in the claims hereinafter appended.

What is claimed is:

1. An inhalation nebulizer comprising:
   an aerosol generator comprising:
      a liquid storage container into which a liquid medicament or a medicament-containing liquid can be filled;
      a diaphragm having a first side and an opposite second side, the diaphragm having a plurality of openings extending therethrough from the first side to the second side, where the first side is connected to the liquid storage container such that a liquid filled into the liquid storage container comes into contact with the first side of the diaphragm; and
      a vibration generator capable of vibrating the diaphragm so that a liquid filled into the liquid storage container is atomized on the second side of the diaphragm through the openings of the diaphragm;
   a mixing chamber into which the aerosol generator expels the aerosol, the mixing chamber in contact with the second side of the diaphragm;
   an inhalation valve that is open to allow an inflow of ambient air into the mixing chamber during an inhalation phase and is closed to prevent escape of the aerosol from the mixing chamber during an exhalation phase; and
   an exhalation valve that is open to allow the discharge of the respiratory air of a patient into the surroundings during the exhalation phase and is closed to prevent the inflow of ambient air during the inhalation phase.

2. The inhalation nebulizer of claim 1, wherein the liquid storage container comprises a single dose container containing a single pre-metered medicament volume.

3. The inhalation nebulizer of claim 1, wherein the liquid storage container comprises a multi dose container containing a plurality of pre-metered medicament volumes.

4. The inhalation nebulizer of claim 1, wherein the liquid storage container comprises a liquid reservoir that is directly fitted into the inhalation nebulizer as a container closure system.

5. The inhalation nebulizer of claim 1, wherein the aerosol produced by the inhalation nebulizer has a mass median aerodynamic diameter between about 1 $\mu$m to about 30 $\mu$m.

6. The inhalation nebulizer of claim 1, wherein the diaphragm forms a part of the wall of the liquid storage container and partially defines the liquid storage container such that a liquid filled into the liquid storage container directly contacts the diaphragm.

7. The inhalation nebulizer of claim 1, wherein the exhalation valve is arranged at a mouthpiece which is removably mounted at the mixing chamber and through which the patient inhales the aerosol from the mixing chamber.

8. The inhalation nebulizer of claim 1, wherein the exhalation valve is arranged in a wall of the mixing chamber.

9. The inhalation nebulizer of claim 1, wherein the inhalation valve is located on the same side of the diaphragm as the liquid storage container.

10. An inhalation nebulizer comprising:
an aerosol generator comprising:
a liquid storage container into which a liquid medicament or a medicament-containing liquid can be filled;
a diaphragm which on one side is connected to the liquid storage container such that a liquid filled into the liquid storage container comes into contact with the one side of the diaphragm; and
a vibration generator capable of vibrating the diaphragm so that a liquid filled into the liquid storage container is atomized on the other side of the diaphragm through the openings of the diaphragm;
a mixing chamber into which the aerosol generator expels the aerosol;
an inhalation valve that is open to allow an inflow of ambient air into the mixing chamber during an inhalation phase and is closed to prevent escape of the aerosol from the mixing chamber during an exhalation phase; and
an exhalation valve that is open to allow the discharge of the respiratory air of a patient into the surroundings during the exhalation phase and is closed to prevent the inflow of ambient air during the inhalation phase,
wherein the liquid storage container is a rotationally symmetrical body, the diaphragm arranged at a front side of the rotationally symmetrical body or cylinder is a circular disk, and the vibration generator is a circular ring surrounding the diaphragm.

11. The inhalation nebulizer of claim 10, wherein the mixing chamber is rotationally symmetrical, and the aerosol diaphragm generator comprises a circular ring disk which is arranged circumferentially at the liquid storage container and which rests upon a projection provided in a cylindrical section of the mixing chamber.

12. The inhalation nebulizer of claim 11, wherein a cap closes the rotationally symmetrical section of the mixing chamber and fixes in position a flexible valve element of the inhalation valve.

13. The inhalation nebulizer of claim 11, wherein the mixing chamber has a cylindrical section.

14. The inhalation nebulizer of claim 10, wherein the diaphragm is arranged perpendicular to the axis of rotation of the rotationally symmetrical section of the mixing chamber.

15. The inhalation nebulizer of claim 10, wherein the diaphragm is arranged inclined to the axis of rotation of the rotationally symmetrical section of the mixing chamber.

16. The inhalation nebulizer of claim 10, wherein the liquid storage container comprises a cylinder.

17. An inhalation nebulizer comprising;
an aerosol generator comprising:
a liquid storage container into which a liquid active agent or a liquid containing an active agent is filled as one of a solution, a suspension and an emulsion;
a diaphragm having a first side and an opposite second side, the diaphragm having a plurality of openings extending therethrough from the first side to the second side, where the first side is connected to the liquid storage container such that a liquid filled into the liquid storage container comes into contact with the first side of the diaphragm; and
a vibration generator capable of vibrating the diaphragm so that a liquid filled into the liquid storage container is atomized on the second side of the diaphragm through the openings of the diaphragm;
a mixing chamber into which the aerosol generator expels the aerosol, the mixing chamber in contact with the second side of the diaphragm;
an inhalation valve that is open to allow an inflow of ambient air into the mixing chamber during an inhalation phase and is closed to prevent escape of the aerosol from the mixing chamber during an exhalation phase; and
an exhalation valve that is open to allow the discharge of the respiratory air of a patient into the surroundings during the exhalation phase and is closed to prevent the inflow of ambient air during the inhalation phase.

18. The inhalation nebulizer of claim 17, wherein the active agent is provided as a submicron suspension.

19. The inhalation nebulizer of claim 17, wherein the active agent is provided as one of a liposome, a nanosome, a microcapsule or a nanocapsule.

20. The inhalation nebulizer of claim 17, wherein the active agent comprises a drug effective against a disease selected from the group of diseases consisting of asthma, chronic obstructive pulmonary disease, lung infections, cystic fibrosis, allergies, pain, migraine, rheumatism, epilepsy, sleeplessness, cancer, diabetes, immune and hormone disorders and gene defects.

21. The inhalation nebulizer of claim 17, wherein the active agent comprises a drug that cannot be administered orally.

22. The inhalation nebulizer of claim 17, wherein the active agent comprises a drug or a combination of drugs for topical or systemic delivery via either a nasal or a pulmonary route.

23. The inhalation nebulizer of claim 17, wherein the active agent comprises an anti-asthmatic.

24. The inhalation nebulizer of claim 17, wherein the active agent comprises an anti-inflammatory drug.

25. The inhalation nebulizer of claim 17, wherein the active agent comprises an antibiotic or an anti-infectiva.

26. The inhalation nebulizer of claim 17, wherein the active agent comprises an anti-tuberculotic.

27. The inhalation nebulizer of claim 17, wherein the active agent is selected from the group of active agents consisting of an anti-epileptic drug, an anti-convulsive drug, an anti-emetic, a pain killer, an anti-rheumatic, an anti-cancer drug, a mucolytic drug, a sleeping assistant, an anti-mycotic, a sexual stimulant, a protein or peptide, heparane and a gene.

28. The inhalation nebulizer of claim 17, wherein the active agent is selected from the group of active agents consisting of an anti-diabetic drug, insulin and a hormone.

29. The inhalation nebulizer of claim 17, wherein the active agent comprises a beta-agonist or an anti-cholinergic.

30. The inhalation nebulizer of claim 17, wherein the active agent is selected from the group of active agents consisting of a corticosteroid, a leukotriene antagonist, a bradykinin antagonist, a cromone, an anti-histamine and an antibody.

31. The inhalation nebulizer of claim 17, wherein the active agent is selected from the group of active agents consisting of an aminoglycoside, a cephalosporine, a macrolide, a chinolone, a nitroimidazol, a glycopeptide, a polyenantibiotic, a beta-lactam, a tetracycline, a quinolone, a sulfonamide, and an azol derivative.

32. The inhalation nebulizer of claim 17, wherein the active agent is selected from the group of active agents consisting of a benzodiazepine, a barbitute and a succinimide.

33. The inhalation nebulizer of claim 17, wherein the active agent comprises sildenafil.

34. The inhalation nebulizer of claim 17, wherein the active agent is selected from the group of active agents consisting of alpha anti-trypsine, erythropoetine, interferones, kinases, elastases, peptides and proteines, which active agents can be administered advantageously via a nasal or pulmonary route.

35. The inhalation nebulizer of claim 17, wherein the active agent is selected from the group of active agents consisting of salbutamol, levalbuterol formoterol, fenoterol, salmeterol, bambuterol, brocaterol, clenbuterol, terbutalin, tolubuterol, epinephrin, isoprenalin, and hexaprenalin.

36. The inhalation nebulizer of claim 17, wherein the active agent is selected from the group of active agents consisting of tiotropium, oxitropium, ipratropium, and glycopyrrolate.

37. The inhalation nebulizer of claim 17, wherein the active agent is selected from the group of active agents consisting of acetylcystein, ambroxol, carbocystein, tyloxapol, dipalmytoylphosphatidylcholin, recombinant surfactant proteins, and D-Nase.

38. The inhalation nebulizer of claim 17, wherein the active agent is selected from the group of active agents consisting of romoglycate, nedocromil, beclomethasone, betamethasone, budesonide, ciclesonide, flunisolide, fluticasone, icomethasone, mometasone, rofleponide, triamcinolone, bradykinine-, prostaglandine-, leucotriene- and platelet activating factor antagonists.

39. The inhalation nebulizer of claim 17, wherein the active agent is selected from the group of active agents consisting of amoxycillin, piperacillin, clavulan acid, sulbactam, ceflaclor, cefazedon, Cefuroxim, Cefoxitin, cefodizim, cefsulodin, cefpodixim, cefixim, imipenem, cilastatin, aztrenonam, streptomycin neomycin, paromomycin, kanamycin, gentamycin, amicacin, tobramycin, spectinomycine, doxycyclin, minocycline, erhytromycine, clarithromycine, roxithromycine, azithromycine, josamycine, spiramycine, Ciprofloxacin, Ofloxacine, Levofloxacine, pefloxacine, lomefloxacine, fleroxacine, clinafloxacine, sitafloxacine, gemifloxacine, balofloxacine, trovafloxacine, moxifloxacine, metronidazol, tinidazol, chloramphenicol, lincomycine, clindamycine, fosfomycine, Vancomycine and Teicoplanine.

40. The inhalation nebulizer of claim 17, wherein the active agent is selected from the group of active agents consisting of rifampicine, isoniacide, cycloserine, terizidone, and ansamycine.

41. The inhalation nebulizer of claim 17, wherein the active agent is selected from the group of active agents consisting of clotrimazol, oxiconazol, miconazol, ketoconazol, itraconazol, fluconazol, amphotericine B, natamycine, nystatine, flucytosine, and Pentamidine.

42. The inhalation nebulizer of claim 17, wherein the active agent is selected from the group of active agents consisting of dimepranol-4-acetate amideo benzoate, thymopentin, interferones, filgrastine, interleukine, azathioprine, and cyclosporine;

virustatics such as podophyllotoxine, vidarabine, tromantadine, zidovudine, and a-anti-trypsin.

43. The inhalation nebulizer of claim 17, wherein the active agent is selected from the group of active agents consisting of corticotropine, tetracosactide, choriogonandotropine, urofolitropine, urogonadotropine, saomatotropine, metergoline, desmopressine, oxytocine, argipressine, ornipressine, leuproreline, triptoreline, gonadoreline, busereline, nafareline, goselerine, somatostatine, parathyroide gland hormones, Dihydrotachysterole, calcitonine, clodron acid, etidron acid, thyroid gland therapeutics, anabolics, androgens, estrogens, gestagenes, and antiestrogenes.

44. The inhalation nebulizer of claim 17, wherein the active agent is selected from the group of active agents consisting of nimustine, melphanlane, carmustine, lomustine, cyclophosphosphamide, ifosfamide, trofosfamide, chlorambucil, busulfane, treosulfane, prednimustine, thiotepa, cytarabine, fluorouracil, methotrexate, mercaptopurine, tioguanine, vinblastine, vincristine, vindesine, alcarubicine, bleomycine, dactinomycine, daunorubicine, doxorubicine, epirubicine, idarubicine, mitromycine, plicamycine, carboplatinum, cis-platinum, titanocendichloride Amsacrine, dacarbazine, estramustine, etoposide, hydroxycarbamide, mitoxanthrone, procarbazine, and temiposide.

45. The inhalation nebulizer of claim 17, wherein the active agent is selected from the group of active agents consisting of Proxibarbal, lisuride, methysergide, dihydroergotamine, ergotamine, clonidine, pizotifene, benzodiazepines, barbiturates, cyclopyrrolones, imidazopyridines, arbiturates, Pheytoin, Primidone, mesuximide, ethosuximide, sultiam, carbamazepin, valproic acid, vigabatrine, Levodopa, carbidopa, benserazide, selegiline, bromocriptine, amantadine, tiapride, Thiethylperazine, bromopride, domperidone, granisetrone, ondoasetrone, tropisetrone, pyridoxine, morphine, codeine, hydromorphone, methadone, fenpipramide, fentanyl, piritramide, pentazocine, buprenorphine, nalbuphine, tilidine, N-methylated barbiturates, thiobarbiturates, ketamine, etomidate, propofol, benzodiazepines, droperidol, haloperidol, alfentanyl, sulfentanyl, tumor necrosis factor alpha and non steroidal anti-inflammatory drugs.

46. The inhalation nebulizer of claim 17, wherein the active agent is selected from the group of active agents consisting of insulin, sulfonylurea derivatives, biguanids, glitizols, glucagon, diazoxid, interleukines, interferones, tumor necrosisfactor (TNF), and colony stimulating factors.

47. The inhalation nebulizer of claim 17, wherein the active agent is selected from the group of active agents consisting of proteins, peptides, heparine, heparinoids, urokinases, streptokinases, ATP-ase, prostacycline, sexual stimulants, and genes, which active agents cannot be administered orally can be delivered advantageously by the inhalation nebulizer either by the nasal or pulmonary route.

48. The inhalation nebulizer of claim 9, further comprising an annular gap surrounding the liquid storage container, such that ambient air passes through the annular gap before reaching the mixing chamber.

* * * * *